(12) United States Patent
Nielsen et al.

(10) Patent No.: US 11,723,378 B2
(45) Date of Patent: *Aug. 15, 2023

(54) *LACTOBACILLUS RHAMNOSUS* WITH INCREASED DIACETYL PRODUCTION

(71) Applicant: Chr. Hansen A/S, Hoersholm (DK)

(72) Inventors: Stina Dissing Aunsbjerg Nielsen, Hoersholm (DK); Helle Skov Guldager, Hoersholm (DK); Cecilie Lykke Marvig Nielsen, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/532,993

(22) Filed: Nov. 22, 2021

(65) Prior Publication Data

US 2022/0151252 A1 May 19, 2022

Related U.S. Application Data

(63) Continuation of application No. 16/757,561, filed as application No. PCT/EP2018/079150 on Oct. 24, 2018, now Pat. No. 11,178,884.

(30) Foreign Application Priority Data

Oct. 27, 2017 (EP) .................................... 17198907

(51) Int. Cl.
*A23C 9/123* (2006.01)
*A23L 29/00* (2016.01)
*A23C 19/032* (2006.01)

(52) U.S. Cl.
CPC ........ *A23C 9/1234* (2013.01); *A23C 19/0323* (2013.01); *A23L 29/065* (2016.08); *A23Y 2220/73* (2013.01)

(58) Field of Classification Search
CPC . A23C 9/1234; A23C 19/0323; A23L 29/065; A23L 27/206; A23L 33/135; A23Y 2220/73; C12R 2001/225
See application file for complete search history.

(56) References Cited

U.S. PATENT DOCUMENTS 9,485,992 B2 11/2016 Hornbaek et al.
10,653,161 B2 5/2020 Jimenez et al.
(Continued)

FOREIGN PATENT DOCUMENTS

| WO | WO-2012/136832 A1 | 10/2012 |
| WO | WO-2013/153074 A1 | 10/2013 |
| WO | WO-2017/037046 A1 | 3/2017 |

OTHER PUBLICATIONS

Aunsbjerg et al., "Contribution of Volatiles to the antifungal effect of *Lactobacillus paracasei* in defined medium and yogurt," International Journal of Food Microbiology, 194, pp. 46-53 (2015) (Published online Nov. 2014).
(Continued)

*Primary Examiner* — Donald R Spamer
*Assistant Examiner* — Jeffrey D Benson
(74) *Attorney, Agent, or Firm* — Foley & Lardner LLP

(57) ABSTRACT

The present invention relates to a composition suitable for preparing a dairy product comprising at least one starter culture and a *Lactobacillus rhamnosus* strain capable of imparting onto the dairy product an enhanced creamy flavor without affecting the rheology negatively, the fermentation time or the post-acidification of the dairy product. The present invention further relates to processes for preparing a dairy product, such as a low-fat yogurt or cheese, which has a high content of diacetyl. A *Lactobacillus rhamnosus* strain useful for preparing such dairy product is also part of the present invention.

13 Claims, 8 Drawing Sheets

(56) References Cited

U.S. PATENT DOCUMENTS

| | | | |
|---|---|---|---|
| 11,178,884 B2 * | 11/2021 | Nielsen | C12P 7/26 |
| 2014/0023749 A1 | 1/2014 | Jimenez et al. | |
| 2018/0249727 A1 | 9/2018 | Nielsen et al. | |
| 2019/0029311 A1 * | 1/2019 | Shin | C12N 11/10 |
| 2019/0059406 A1 | 2/2019 | Nielsen et al. | |

OTHER PUBLICATIONS

Jyoti et al., "Diacetyl production and growth of *Lactobacillus rhamnosus* on multiple substrates," World Journal of Microbiology & Biotechnology 19: 509-514 (2003).

* cited by examiner

LACTOBACILLUS RHAMNOSUS WITH INCREASED DIACETYL PRODUCTION

CROSS-REFERENCE TO RELATED APPLICATIONS

The present application is a continuation of U.S. application Ser. No. 16/757,561, filed Apr. 20, 2020, which is the U.S. National Stage of International Application No. PCT/EP2018/079150, filed Oct. 24, 2018, and claims priority to European Patent Application No. 17198907.2, filed Oct. 27, 2017.

FIELD OF THE INVENTION

The present invention relates to a composition suitable for preparing a dairy product comprising a *Lactobacillus rhamnosus* strain capable of imparting onto the dairy product an enhanced creamy flavor by means of a high production of diacetyl without affecting negatively the rheology of the dairy product. The composition of the invention may be used together with or as a part of a starter culture for producing a dairy product. The present invention further relates to processes for preparing a dairy product, such as a low-fat yogurt, cheese and sour cream, which has a high content of diacetyl. A *Lactobacillus rhamnosus* strain useful for preparing such dairy products is also part of the present invention.

BACKGROUND ART

WO2012/136830 discloses an anti-fungal *Lactobacillus rhamnosus* strain for producing a dairy product.

In the dairy industry products with a low or no fat content are experiencing increasing demand from consumers. However, such low fat dairy products often experience a lack of creamy flavor.

Diacetyl is a high value product and it is used in the dairy industry as a buttery flavor-producing compound added to such products as margarines and oil-based products.

Heterolactic acid bacteria form diacetyl/acetoin as a by-product along with lactate as the main product. The cells form active acetaldehyde from pyruvate and thiamine pyrophosphate by pyruvate oxidase. The active acetaldehyde condenses with another molecule of pyruvate and forms alpha-acetolactate synthase. Formation of diacetyl in *Lactobacillus rhamnosus* is not well understood—in *Lactococcus lactis* subsp. *lactis* biovar. diacetylactis it has been suggested that alpha-acetolactate is oxidized to diacetyl by an alpha acetolactate oxidase (Jyoti et al 2003). Acetoin is formed directly by decarboxylation of alpha-acetolactate. Acetoin formation may also occur by the irreversible diacetyl reductase of diacetyl into acetoin.

*Lactobacillus rhamnosus* is a heterolactic acid bacterium which can be used to produce flavor compounds like diacetyl and acetoin (Jyoti et al. 2003). The level of diacetyl produced depends on the strain as well as the substrate on which it is grown.

U.S. Pat. Nos. 4,867,992 and 5,236,833 relate to processes for production of diacetyl by fermenting a coffee substrate and a pectin substrate, respectively, with a lactic acid producing bacteria.

The preparation, concentration and addition of diacetyl and/or acetoin to food products are connected with substantial costs.

U.S. Pat. No. 4,678,673 is directed to oilseed products fermented with a *Lactobacillus rhamnosus* strain which produces diacetyl and acetoin. The fermented oilseed products have a buttery or dairy-like flavor. There is no mention of use of *Lactobacillus rhamnosus* in dairy products.

WO2012/136832 discloses a diacetyl-producing *Lactobacillus rhamnosus* strain for producing a dairy product.

There exists a need for providing lactic acid bacteria for producing dairy products with an increased production of diacetyl.

SUMMARY OF THE INVENTION

It is an object of the present invention to provide a composition and a method for preparing a dairy product improved with an enhanced creamy flavor imparted by the presence of a strain of *Lactobacillus rhamnosus*.

It is another object of the present invention to provide a novel *Lactobacillus rhamnosus* strain with improved properties in relation to being able to give an enhanced creamy flavor to a dairy product, such as a yogurt or cheese.

Additional objects will become apparent hereinafter and still others will be obvious to one skilled in the art to which the invention pertains.

As can be seen in the working examples herein, the described *Lactobacillus rhamnosus* strain CHCC15871 that was deposited with the German Collection of Microorganisms and Cell Cultures (DSMZ) under the accession no. DSM 32666 produces diacetyl and acetoin thereby giving enhanced creamy flavor to a dairy product, without significantly affecting the rheology and the post-acidification of the dairy product.

Also, it has surprisingly been found that the *Lactobacillus rhamnosus* strain CHCC15871 of the invention in addition to its high diacetyl producing activity has high anti-fungal activity. In particular, *Lactobacillus rhamnosus* strain CHCC15871 of the invention has an increased activity against the growth of yeast as compared to conventional anti-fungal *Lactobacillus rhamnosus* strains.

Accordingly, a first aspect of the present invention relates to a composition comprising the *Lactobacillus rhamnosus* strain CHCC15871 that was deposited with the German Collection of Microorganisms and Cell Cultures (DSMZ) under accession no. DSM 32666 or a mutant strain thereof, wherein the mutant strain is obtained by using the deposited strain as mother strain and wherein the mutant strain has the same or a higher diacetyl production as compared to the mother strain.

A second aspect of the present invention relates to use of a composition according to the first aspect of the present invention for preparing a dairy product.

A third aspect of the present invention is directed to a method for producing a dairy product, the method comprising the steps:
a) inoculating a milk substrate with the composition according to the first aspect of the present invention;
b) fermenting the milk substrate;
c) optionally adding further microorganisms and/or additives to the milk substrate;
d) optionally post-treating the milk substrate; and
e) optionally packaging the dairy product.

A fourth aspect of the invention relates to a dairy product obtainable by the method according to the third aspect of the invention.

A fifth aspect of the present invention relates to a *Lactobacillus rhamnosus* CHCC15871 strain that was deposited with the German Collection of Microorganisms and Cell Cultures (DSMZ) under accession no. DSM 32666 or a mutant strain thereof, wherein the mutant strain is obtained by using the deposited strain as mother strain, and wherein the mutant strain has the same or a higher diacetyl production as compared to the mother strain.

DETAILED DESCRIPTION OF THE INVENTION

Definitions

Figure 1:
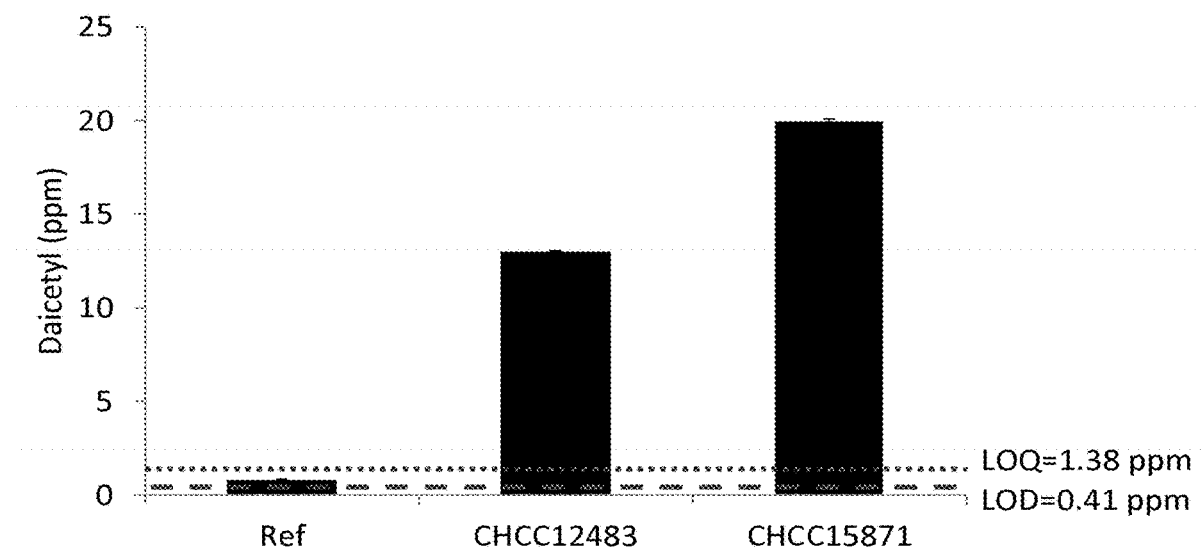
FIG. 1 shows diacetyl levels after storage at 7±1° C. for 14 days in fermented milk products fermented with starter culture alone (Reference), or starter cultures in combination with Lb. rhamnosus CHCC12483 or together with Lb. rhamnosus CHCC15871. LOD: Limit of detection. LOQ: Limit of quantification.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes Lactococcus spp., Streptococcus spp., Lactobacillus spp., Leuconostoc spp., Pseudoleuconostoc spp., Pediococcus spp., Brevibacterium spp., Enterococcus spp. and Propionibacterium spp. Additionally, lactic acid producing bacteria belonging to the group of the strict anaerobic bacteria, bifidobacteria, i.e. Bifidobacterium spp., are generally included in the group of lactic acid bacteria. These are frequently used as food cultures alone or in combination with other lactic acid bacteria.

Lactic acid bacteria, including bacteria of the species Lactobacillus spp. and Streptococcus thermophilus, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product or a cheese. Such lactic acid bacterial cultures are in general referred to as "starter cultures" or "starters".

The term "mesophile" herein refers to microorganisms that thrive best at moderate temperatures (15° C.-40° C.). The industrially most useful mesophilic bacteria include Lactococcus spp. and Leuconostoc spp. The term "mesophilic fermentation" herein refers to fermentation at a temperature between about 12° C. and about 35° C. The term "mesophilic dairy product" refers to dairy products prepared by mesophilic fermentation of a mesophilic starter culture and include such dairy products as buttermilk, sour milk, cultured milk, smetana, sour cream and fresh cheese, such as quark, tvarog and cream cheese.

The term "thermophile" herein refers to microorganisms that thrive best at temperatures above 43° C. The industrially most useful thermophilic bacteria include Streptococcus spp. and Lactobacillus spp. The term "thermophilic fermentation" herein refers to fermentation at a temperature above about 35° C. The term "thermophilic dairy product" refers to dairy products prepared by thermophilic fermentation of a thermophilic starter culture and include such dairy products as yogurt.

The term "milk" is to be understood as the lacteal secretion obtained by milking any mammal, such as cows, sheep, goats, buffaloes or camels. In a preferred embodiment, the milk is cow's milk. The term milk also includes protein/fat solutions made of plant materials, e.g. soy milk.

The term "milk substrate" may be any raw and/or processed milk material that can be subjected to fermentation according to the method of the invention. Thus, useful milk substrates include, but are not limited to, solutions/suspensions of any milk or milk-like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of dairy products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid (such as a cheese) or liquid form (such as a fermented milk product).

In the present context, the term "shear stress" determines viscosity. Viscosity (unit is Pa s) is defined as Shear Stress (Pa)/Shear rate (1/s).

Shear stress value is reported as a standard herein at shear rate=300 1/s. Sensory experiments have shown (data not shown) that the best correlation between rheological measurements and sensory viscosity/mouth thickness are found when using the viscosity measured at shear rate 300 1/s.

In connection with the present invention the term "shear stress" means shear stress as measured by the following method:

Seven days after incubation, the fermented milk product was brought to 13° C. and manually stirred gently by means of a stick fitted with a perforated disc until homogeneity of the sample. The rheological properties of the sample were assessed on a rheometer (Anton Paar Physica Rheometer with ASC, Automatic Sample Changer, Anton Paar® GmbH, Austria) by using a bob-cup. The rheometer was set to a constant temperature of 13° C. during the time of measurement.

Settings were as follows:
Holding time (to rebuild to somewhat original structure)
5 minutes without any physical stress (oscillation or rotation) applied to the sample.
Oscillation step (to measure the elastic and viscous modulus, G' and G", respectively, therefore calculating the complex modulus G*)
Constant strain=0.3%, frequency (f)=[0.5 . . . 8] Hz
6 measuring points over 60 s (one every 10 s)
Rotation step (to measure shear stress at 300 1/s)
Two steps were designed:
Shear rate=[0.3–300] 1/s and 2) Shear rate=[275–0.3] 1/s.
Each step contained 21 measuring points over 210 s (on every 10 s).

The shear stress at 300 1/s was chosen for further analysis, as this correlates to mouth thickness when swallowing a fermented milk product.

In the present context, the term "mutant" should be understood as a strain derived from a strain of the invention by means of e.g. genetic engineering, radiation, UV light, and/or chemical treatment and/or methods that induce changes in the genome. It is preferred that the mutant is a functionally equivalent mutant, e.g. a mutant that has substantially the same, or improved, properties (e.g. regarding diacetyl production, viscosity, gel stiffness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. In particular, the mutant is a natural mutant, i.e. a mutant e.g. obtained by subjecting the mother strain to a mutagenization treatment comprising growing the mother strain in a medium devoid of one or more conventional growth factors, also referred to as selection pressure. In this connection the term "natural mutant" means a mutant, which has not been obtained by using genetic engineering, radiation, UV light, and/or chemical treatment. A mutant may have been subjected to several mutagenization treatments (a single treatment should be understood as containing one mutagenization step followed by a screening/selection step), but it is presently preferred that no more than 20, or no more than 10, or no more than 5, treatments (or screening/selection steps) are carried out. In a presently preferred mutant, less than 5%, or less than 1% or even less than 0.1% of the nucleotides in the bacterial genome have been shifted with another nucleotide, or deleted, compared to the mother strain. In a particular embodiment, the mutant contains no more than 20, in particular no more than 10, in particular no more than 5, in particular no more than 4, in particular no more than 3, in particular no more than 2, and in particular no more than 1 nucleotide mutation of the bacterial genome as compared to the mother strain, wherein a mutation is a substitution, an insertion or a deletion of one nucleotide.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Composition of the Invention

The inventors of the present invention have surprisingly discovered that by inoculating and fermenting a milk substrate with a strain of Lactobacillus rhamnosus in addition to a starter culture it is possible to impart onto the resulting dairy product a pleasant creamy flavor without negatively affecting the texture of the dairy product, the fermentation time and post-acidification.

The enhanced creamy flavor was detected in dairy products prepared both by mesophilic and thermophilic fermentation processes in the presence of a Lactobacillus rhamnosus CHCC15871 that was deposited with the German Collection of Microorganisms and Cell Cultures (DSMZ) under accession no. DSM 32666.

By the term "enhanced creamy flavor" is meant that the content of diacetyl and/or acetoin in the product is increased and/or that the creamy flavor of the product as determined by a sensory panel is enhanced compared to a product which does not comprise a Lactobacillus rhamnosus strain according to the present invention.

Without wishing to be bound by theory, it is believed that the enhanced creamy flavor imparted to the dairy product by a Lactobacillus rhamnosus strain according to the present invention is due to the enhanced production of diacetyl and/or acetoin by the Lactobacillus rhamnosus strain.

The dairy product in a preferred embodiment is a low/no fat fermented milk product or cheese which essentially lacks a creamy flavor when a Lactobacillus rhamnosus strain according to the present invention has not been used in the fermentation or has not been used in the fermentation.

In a particular embodiment of the invention, the composition comprises at least one further lactic acid bacterium.

In a particular embodiment of the composition of the invention, the further lactic acid bacterium is at least one anti-fungal lactic acid bacterium selected from the group consisting of a Lactobacillus rhamnosus strain, a Lactobacillus fermentum strain, a Lactobacillus paracasei strain, a Lactobacillus plantarum strain, a Propionibacterium freudenreichii strain, e.g. Propionibacterium freudenreichii subsp. shermanii, a Propionibacterium thoenii strain, a Propionibacterium jensenii strain, a Pediococcus acidilactici strain, a Enterococcus faecium strain, a Lactococcus lactis strain, and a Lactobacillus amylovorus. In this embodiment the composition is suitable for use for adding together with a starter culture to a milk substrate in a process for producing a dairy product, such a fermented milk product, e.g. a yogurt or sour cream, or a cheese, at the start of the fermentation in order to increase the diacetyl content and/or to obtain an anti-fungal effect in the fermented product or cheese. Alternatively, the composition may be added during the course of the fermentation, i.e. after the start and before the end of the fermentation.

In a particular embodiment of the composition of the invention, the at least one antifungal lactic acid bacterium is the Lactobacillus rhamnosus strain CHCC15860 that was deposited at German Collection of Microorganisms and Cell Cultures (DSMZ) under the accession No.: 32092.

In a particular embodiment of the invention, the composition comprises a starter culture for producing a fermented milk product comprising one or more strains selected from the group consisting of the genera Lactococcus, Streptococcus and Lactobacillus.

Typically, such a composition comprises the bacteria in a concentrated form including frozen, dried or freeze-dried concentrates typically having a concentration of viable cells, which is in the range of $10^4$ to $10^{12}$ cfu (colony forming units) per gram of the composition including at least $10^4$ cfu per gram of the composition, such as at least $10^5$ cfu/g, e. g. at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g. Thus, the antimicrobial composition of the invention is preferably present in a frozen, dried or freeze-dried form, e.g. as a Direct Vat Set (DVS) culture. However, as used herein the antimicrobial composition may also be a liquid that is obtained after suspension of the frozen, dried or freeze-dried cell concentrates in a liquid medium such as water or PBS buffer. Where the antimicrobial composition of the invention is a suspension, the concentration of viable cells is in the range of $10^4$ to $10^{12}$ cfu (colony forming units) per ml of the composition including at least $10^4$ cfu per ml of the composition, such as at least $10^5$ cfu/ml, e.g. at least $10^6$ cfu/ml, such as at least $10^7$ cfu/ml, e.g. at least $10^8$ cfu/ml, such as at least $10^9$ cfu/ml, e.g. at least $10^{10}$ cfu/ml, such as at least $10^{11}$ cfu/ml.

The composition may additionally contain as further components cryoprotectants and/or conventional additives including nutrients such as yeast extracts, sugars and vitamins, e.g. vitamin A, C, D, K or vitamins of the vitamin B family. Suitable cryoprotectants that may be added to the compositions of the invention are components that improve the cold tolerance of the microorganisms, such as mannitol, sorbitol, sodium tripolyphosphate, xylitol, glycerol, raffinose, maltodextrin, erythritol, threitol, trehalose, glucose and fructose. Other additives may include carbohydrates, flavors, minerals, enzymes (e.g. rennet, lactase and/or phospholipase).

As it is normal in lactic acid bacterial fermentation processes to apply a mixed culture as a starter culture, the composition will in certain embodiments comprise a multiplicity of strains either belonging to the same species or belonging to different species. A typical example of such a useful combination of lactic acid bacteria in a thermophilic starter culture is a mixture of a Lactobacillus bulgaricus strain and a Streptococcus thermophilus strain. A typical example of such a useful combination of lactic acid bacteria in a mesophilic starter culture is a mixture of a Lactococcus lactis strain in combination with a strain selected from the group consisting of a Leuconostoc strain, a Lactococcus lactis subsp. lactis biovar. diacetylactis strain and a Streptococcus thermophilus strain.

In a preferred embodiment of the present invention the starter culture is a thermophilic starter culture and the composition is suitable for thermophilic fermentation.

In another preferred embodiment the starter culture is selected from the group consisting of the genera Streptococcus and Lactobacillus. The starter culture in a preferred embodiment comprises at least one Lactococcus lactis strain. The starter culture may comprise any Lactococcus lactis strain known in the art, such as strains from the

*Lactococcus lactis* subsp. *cremoris*, *Lactococcus lactis* subsp. *hordniae* or *Lactococcus lactis* subsp. *lactis*. In yet another preferred embodiment the starter culture comprises a *Lactococcus lactis* subsp. *cremoris* strain and a *Lactococcus lactis* subsp. *lactis* strain.

The composition can be used for preparing a dairy product with enhanced creamy flavor.

In a preferred embodiment the dairy product is a fermented milk product, such as yogurt. In another preferred embodiment the dairy product is a cheese.

In a preferred embodiment the dairy product contains at least 1.0 ppm of diacetyl, in particular at least 3.0 ppm of diacetyl, more in particular at least 5.0 ppm of diacetyl, more in particular at least 7.0 ppm of diacetyl, more in particular at least 9.0 ppm of diacetyl, more in particular at least 11.0 ppm of diacetyl, more in particular at least 13.0 ppm of diacetyl, more in particular at least 15.0 ppm of diacetyl, more in particular at least 17.0 ppm of diacetyl, and most in particular at least 19.0 ppm of diacetyl.

The skilled person will be aware of numerous methods to determine the content of diacetyl in the dairy products of the invention. For example, the content may be determined by suitable chromatographic methods, such as static head space gas chromatography (HSGC). The secretion of diacetyl can be determined using different assays known in the art, but is preferably determined in an assay comprising:
(1) preparing a fermented milk product by:
  (a) inoculating a milk with the *Lactobacillus rhamnosus* in a concentration of at least $5\times10^6$ CFU/g and with a starter culture,
  (b) fermenting until a target pH, e.g. a pH of 4.6, is reached, and;
(2) storing the fermented milk product at $7\pm1°$ C. for 14 days;
(3) adding 200 µl of 4N $H_2SO_4$ to 1 g of the fermented milk product and determining the concentration of diacetyl by static head space gas chromatography.

Anti-Fungal Composition of the Invention

In a particular embodiment, the composition of the invention is an anti-fungal composition comprising the *Lactobacillus rhamnosus* CHCC15871 of the invention and at least one further anti-fungal lactic acid bacterium.

In a preferred embodiment the compositions of the invention are used against fungi, such as yeasts and molds. This means that the compositions are used for inhibiting and/or preventing the growth of fungi which cause contamination in dairy industry processes, in particular milk fermentation processes. The compositions of the present invention can be used, e.g., for inhibiting and/or preventing the growth of yeasts, such as yeasts of the genera *Klyveromyces* (e.g., *K. marxianus*, *K. lactis*), *Pichia* (e.g., *P. fermentans*), *Yarrowia* (e.g., *Y. lipolytica*), *Candida* (e.g., *C. sake*), *Debaryomyces* (e.g., *D. hansenii*) and the like; or molds, such as molds from the genera *Penicillium* (e.g., *P. nalgiovense*, *P. commune*, *P. crustosum*, *P. brevicompactum*, *P. glabrum*), *Mucor* spp., *Cladiosporium* ssp., *Aspergillus* (e.g., *A. versicolor*) and the like. It is especially preferred to use the compositions of the invention to inhibit and/or prevent growth of the species *Klyveromyces marxianus*, *Yarrowia lipolytica*, *Penicillium nalgiovense*, *Cladiosporium* ssp., *Penicillium commune*, *Mucor* ssp., *Penicillium brevicompactum*, *Aspergillus versicolor*, *Penicillium crutosum*, *Kluyveromyces lactis*, and/or *Debaryomyces hansenii*.

In a particular embodiment of the invention the antifungal activity of the *Lactobacillus rhamnosus* CHCC15871 strain may be measured as the ability to inhibit the growth of the fungus *Penicillium solitum* deposited under the accession No.: DSM 32093 or the growth of the fungus *Penicillium brevicompactum* deposited under the accession No.: DSM 32094 or the growth of *Penicillium crutosum*.

In the context of the present invention the ability to inhibit the growth of the fungus *Penicillium solitum* deposited under the accession No.: DSM 32093 or the growth of the fungus *Penicillium brevicompactum* deposited under the accession No.: DSM 32094 is preferably determined using an assay comprising:
(1) preparing a fermented milk product by:
  (a) inoculating a milk with the *Lactobacillus rhamnosus* CHCC15871 in a concentration of at least $5\times10^6$ CFU/g and with a starter culture,
  (b) fermenting until a target pH, e.g. a pH of 4.6, is reached, and
  (c) solidifying the fermented milk by the addition of agar;
(2) generating at least one spot of the *P. solitum* or the *P. brevicompactum* on the agar solidified fermented milk with a concentration of 500 spores/spot and incubating the same for 7 days at 25° C.;
(3) determining the percent inhibition by determining the largest diameter of the colony formed by growth of the *P. solitum* or *P. brevicompactum* and expressing the diameter as percent of the largest diameter formed under the same conditions but in the absence of the *Lactobacillus rhamnosus* strain.

In a particular embodiment of the invention the antifungal activity of the *Lactobacillus rhamnosus* CHCC15871 strain is measured as the ability to inhibit the growth of one or more yeasts selected form the group consisting of *Torulaspora delbrueckii*, *Cryptococcus fragicola*, *Debaryomyces hansenii*, *Yarrowia lipolytica*, *Rhodotorula mucilaginosa*, *Pichia quilermondii*, and *Candida* spp, preferably one or more yeasts selected from the group consisting of *Torulaspora delbrueckii*, *Cryptococcus fragicola*, *Debaryomyces hansenii*, *Yarrowia lipolytica*, and *Rhodotorula mucilaginosa*.

In the context of the present invention the ability to inhibit the growth of the one or more yeasts selected from the group consisting of *Torulaspora delbrueckii*, *Cryptococcus fragicola*, *Debaryomyces hansenii*, *Yarrowia lipolytica*, and *Rhodotorula mucilaginosa* is preferably determined using an assay comprising:
(1) preparing a fermented milk product by:
  (a) inoculating a milk with the *Lactobacillus rhamnosus* CHCC15871 in a concentration of at least $5\times10^6$ CFU/g and with a starter culture,
  (b) fermenting until a target pH, e.g. a pH of 4.6, is reached, and
  (c) solidifying the fermented milk by the addition of agar;
(2) generating at least one spot of the four yeasts *Torulaspora delbrueckii*, *Cryptococcus fragicola*, *Debaryomyces hansenii*, and *Yarrowia lipolytica* on the agar solidified fermented milk with concentrations of $10^3$, $10^2$ and $10^1$ CFU/spot and incubating the same for 27 days at 7° C.;
(3) determining the percentage of inhibition by determining the number of the 12 spots where growth occur (from 0 to 12 spots) for the plate containing *Lactobacillus rhamnosus* CHCC15871 with the starter culture and expressing the number as percentage of the number of spots where growth occur for the plate containing the starter culture only.

In an alternative embodiment step (3) is carried out as a qualitative determination by visual inspection and comparison of the plates and assessing the level of inhibition by comparing the plates with respect to 1) the number of spots with no growth and 2) for the spots with growth, the level of growth (diameter, density and thickness of spot).

Use According to the Invention

As mentioned above the invention further relates to the use of the composition of the invention for preparing a dairy product.

In a particular embodiment the dairy product is a fermented milk product. In a particular embodiment the fermented milk product is a yogurt. In another particular embodiment the dairy product is a cheese.

In a particular embodiment the dairy product comprises at least 0.75 ppm of diacetyl in particular at least 1.5 ppm of diacetyl.

The present invention further relates to the use of the composition of the invention for producing diacetyl in a process for preparing a dairy product.

The present invention further relates to the use of the composition of the invention for inhibiting growth of fungi in a process for preparing a dairy product. The present invention further relates to the use of the composition of the invention for inhibiting growth of yeast in a process for preparing a dairy product.

Method of the Invention

As said above, an aspect of the invention relates to a method of manufacturing a dairy product with a creamy flavor comprising:
a) inoculating a milk substrate with the composition according to the first aspect of the invention;
b) fermenting the milk substrate;
c) optionally adding further microorganisms and/or additives to the milk substrate;
d) optionally post-treating the milk substrate; and
e) optionally packaging the dairy product.

As described above, the milk substrate to be used in step a) may be any raw and/or processed milk material that can be subjected to fermentation according to the method of the invention.

The milk substrate may be inoculated with the above composition by any suitable method. For example, the milk substrate may be inoculated by direct inoculation into a fermentation vessel.

In one preferred embodiment step b) comprises fermenting the milk substrate at a temperature above about 37° C., preferably at a temperature of between about 38° C. to about 45° C., and more preferably between about 39° C. to about 42° C. In another preferred embodiment step b) comprises fermenting the milk substrate at a temperature of between about 22° C. to about 34° C., more preferably between about 24° C. to about 32° C., and more preferably between about 26° C. to about 30° C.

Fermentation processes to be used in production of dairy products are well known and the person of skill in the art will know how to select suitable process conditions, such as temperature, oxygen, amount and characteristics of microorganism(s) and process time. Obviously, fermentation conditions are selected so as to obtain a fermented milk product suitable in the production of a dairy product with improved flavor and high texture.

Further microorganisms and/or additives may be added to the milk substrate before, during or after fermentation of the milk substrate in step b). Microorganisms that may be added to the milk substrates will contribute in an advantageous manner to the properties of the dairy product. For example, the microorganism may improve or support the diacetyl production, the viscosity, gel stiffness, mouth coating, flavor, post acidification, and/or acidification speed in the dairy product. Optionally, other ingredients may be added to the milk substrate, such as colors, stabilizers, e.g., pectin, starch, modified starch, CMC, etc.; or polyunsaturated fatty acids, e.g. omega-3 fatty acids. Such ingredients may be added at any point during the production process, e.g. before or after fermentation.

The milk substrate may further be post-treated by any means necessary to create the desired dairy product. For example, further components, such conventional additives including nutrients such as sugars and vitamins, may be added to the milk substrate. Further, the milk substrate may e.g. be homogenized or treated with heat, i.e. pasteurized.

The dairy product may be packaged in any suitable manner known in the art. For example, the dairy product may be packaged in a sealed container having a volume in the range of e.g. 25 to 1500 ml. The product may be packaged at any point during the production process, e.g. packaged next to the inoculating step and then fermented in the package.

The dairy products, which are obtained by the method, include as typical examples products such as yogurt, sour cream, cheese and buttermilk.

A dairy product obtainable by the method above is also part of the present invention.

In a preferred embodiment the dairy product is a fermented milk product. "Fermented milk product" as used herein includes but is not limited to products such as thermophilic fermented milk products, e.g. yogurt, mesophilic fermented milk products, e.g. sour cream and buttermilk, 0 as well as fermented whey.

The term "thermophilic fermented milk product" refers to fermented milk products prepared by thermophilic fermentation of a thermophilic starter culture and include such fermented milk products as set-yogurt, stirred-yogurt and drinking yogurt, e.g. Yakult.

The term "mesophilic fermented milk product" refers to fermented milk products prepared by mesophilic fermentation of a mesophilic starter culture and include such fermented milk products as buttermilk, sour milk, cultured milk, smetana, sour cream, Kefir and fresh cheese, such as quark, tvarog and cream cheese.

In yet another preferred embodiment the dairy product is a cheese, such as a Cottage, Feta, Cheddar, Parmesan, Mozzarella, Emmentaler, Danbo, Gouda, Edam, Feta-type, blue cheese, brine cheese, Camembert or Brie.

In a preferred embodiment the dairy product contains at least 0.75 ppm of diacetyl, such as at least 1.0 ppm of diacetyl, such as at least 1.5 ppm of diacetyl.

Strain CHCC15871 of the Invention

The fifth aspect of the invention relates to the *Lactobacillus rhamnosus* CHCC15871 strain that was deposited with the German Collection of Microorganisms and Cell Cultures (DSMZ) under the accession no. DSM 32666. Apart from this strain, the invention also pertains to mutants that have been derived from it, i.e. they have been obtained by using the deposited strain CHCC15871 as a mother strain. The mutant strain may be derived from CHCC15871, e.g., by means of genetic engineering, radiation, UV light, chemical treatment and/or methods that induce changes in the genome. A mutant according to the invention will essentially have the same characteristics as the mother strain in terms of the production levels of acetate, acetaldehyde, diacetyl and/or acetoin. It is preferred that the mutant produces essentially at least 80% or more, at least 90% or more, at least 95% or more, or at least 100% or more of acetate, acetaldehyde, diacetyl and/or acetoin compared with its mother strain.

In connection with the present invention the expression "same or a higher diacetyl production as compared to the mother strain" means a diacetyl production of at least 100% as compared to the mother strain.

It is clear for the skilled person that by using the deposited strain as mother strain, the skilled reader can by conventional mutagenesis or re-isolation techniques routinely obtain further mutants or derivatives thereof that retain the herein described relevant features and advantages. Accordingly, the term "a mutant thereof" of the first aspect relates to mutant strains obtained by using the deposited strain as mother strain.

Embodiments of the present invention are described below, by way of non-limiting examples.

EXAMPLES

Example 1: Semi-Quantitative Analysis of the Inhibitory Effect of Lb. Rhamnosus CHCC15871 Against Different Yeast and Mold Contaminants, and Diacetyl Production For the semi-quantitative analysis of the inhibitory effect of Lb. rhamnosus CHCC15871, an agar-assay was used, resembling the manufacturing process and product of yoghurt:

Reduced-fat (1.5% w/v) homogenized milk was heat-treated at 90±1° C. for 20 min and cooled immediately. A commercial yogurt starter culture (F-DVS YoFlex Mild 2.0) was inoculated at 0.02% (v/w), and the inoculated milk was distributed into 200 ml bottles. One bottle was inoculated with Lb. rhamnosus CHCC15871 in total concentration of $1 \times 10^7$ CFU/g, one bottle was inoculated with Lb. rhamnosus CHCC12483, and the commercial bioprotective strain (isolated from Holdbac® YM-B) in total concentration of $1 \times 10^7$ CFU/g, one bottle was inoculated with an Lb. rhamnosus comparative strain with antifungal activity, and one bottle was used as a reference and only inoculated with the starter culture. All bottles were incubated in a water bath at 43±1° C. and fermented at these conditions until pH of 4.60±0.1 was reached. After fermentation, the bottles were vigorously shaken to break the coagulum and cooled on ice. Then the fermented milk was warmed to a temperature of 40° C. and added 40 ml of a 5% sterile agar solution that had been melted and cooled down to 60° C. This solution of fermented milk and agar was then poured into sterile Petri dishes and the plates were dried in a LAF bench for 30 min.

Spore suspension of three different molds were spotted in concentration of 500 spores/spot; Penicillium brevicompactum (DSM 32094), P. crustosum, P. solitum (DSM 32093). The three molds were spotted on the same plate. Plates were incubated at 25±1° C. and regularly examined for the growth of molds. Five yeasts including Torulaspora delbrueckii, Cryptococcus fragicola, Debaryomyces hansenii, Yarrowia lipolytica and Rhodotorula mucilaginosa were spotted in concentrations of $10^3$, $10^2$ and $10^1$ CFU/spot. Plates were incubated at 7±1° C. and regularly examined for the growth of yeast.

On day 14 samples were analyzed for diacetyl by static head space gas chromatography (HSGC), a sensitive method for analyzing volatiles in complex matrices. The setup consisted of a Static Head Space sampler connected to Gas Chromatograph with Flame Ionization Detector (FID). For that purpose the following equipment was used:

HS-autosampler: HS40XI, TurboMatrix 110, Perkin Elmer.
HS-software: HSControl v.2.00, Perkin Elmer.
GC: Autosystem XL, Perkin Elmer.
GC-software: Turbochrom navigator, Perkin Elmer.
Column: HP-FFAP 25 m×0.20 mm×0.33 pin, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 µl of 4N $H_2SO_4$ to 1 g yoghurt sample and immediately analyzed by HSGC.

The effect on diacetyl production is illustrated in FIG. 1, showing that addition of Lb. rhamnosus CHCC15871 during milk fermentation produce much higher levels of diacetyl when compared to commercially available Lb. rhamnosus strain.

Figure 2:
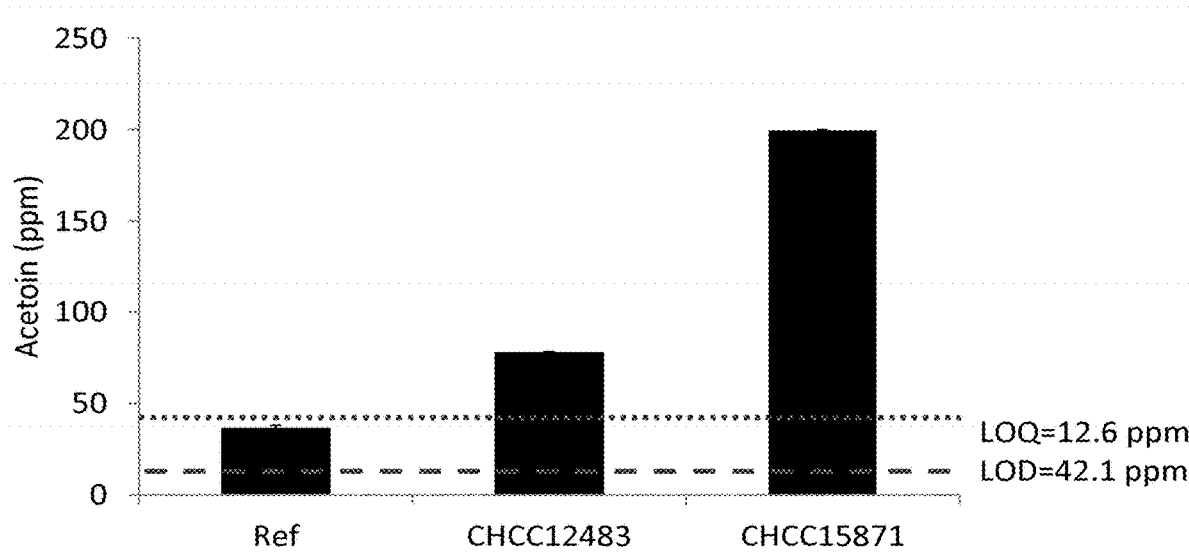
FIG. 2 shows acetoin levels after storage at 7±1° C. for 14 days in fermented milk products fermented with starter culture alone (Reference), or starter cultures in combination with Lb. rhamnosus CHCC12483 or together with Lb. rhamnosus CHCC15871. LOD: Limit of detection. LOQ: Limit of quantification.

The effect on acetoin production is illustrated in FIG. 2, showing that addition of Lb. rhamnosus CHCC15871 during milk fermentation produce much higher levels of acetoin when compared to commercially available Lb. rhamnosus strain.

Figure 3:
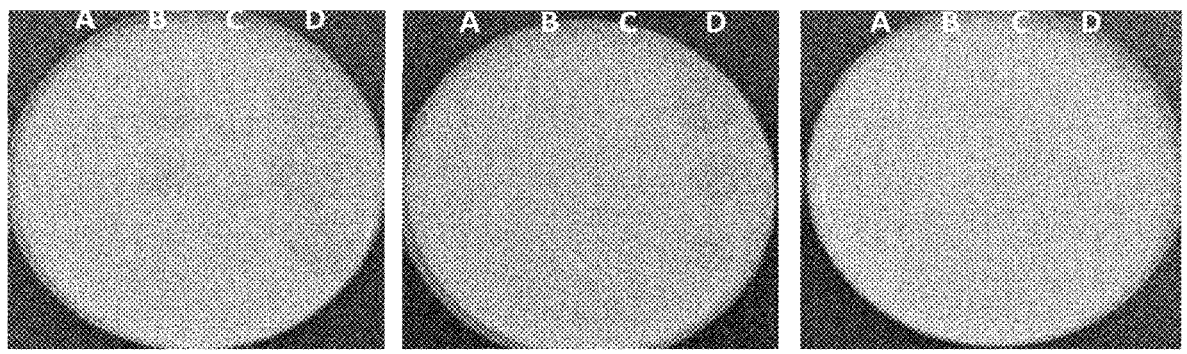
FIG. 3 shows the growth of yeast on plates prepared from milk fermented with a starter culture alone (reference, first plate), together with Lb. rhamnosus CHCC12483 (second plate), or together with Lb. rhamnosus CHCC15871 (third plate) for 4 different yeast contaminants A, B, C and D and for three concentrations of yeast (top, middle and bottom row).

FIG. 3 shows the growth of yeast on plates prepared from milk fermented with a starter culture alone (reference, first plate), together with Lb. rhamnosus CHCC12483 (second plate), or together with Lb. rhamnosus CHCC15871 (third plate). The plates had been incubated at 7±1° C. for 27 days. The target contaminants were added in concentrations of $1 \times 10^3$ cfu/spot (top row), $1 \times 10^2$ cfu/spot (middle row) and $1 \times 10^1$ cfu/spot (bottom row): (A) Torulaspora delbrueckii, (B) Cryptococcus fragicola, (C) Debaryomyces hansenii and (D) Yarrowia lipolytica.

Figure 4:
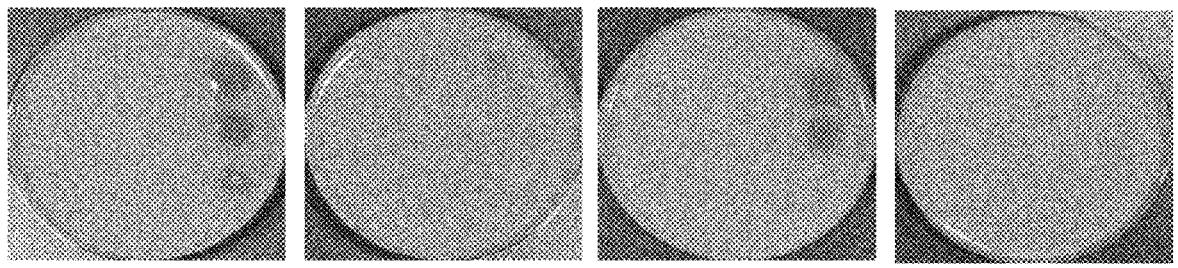
FIG. 4 shows the growth of yeast on plates prepared from milk fermented with a starter culture alone (reference, first plate), together with Lb. rhamnosus CHCC12483 (second plate), together with a Lb. rhamnosus comparative strain (third plate) or together with Lb. rhamnosus CHCC15871 (fourth plate) for one yeast contaminant and for three concentrations of yeast (top, middle and bottom row).

FIG. 4 shows the growth of yeast on plates prepared from milk fermented with a starter culture alone (reference, first plate), together with Lb. rhamnosus CHCC12483 (second plate), together with the Lb. rhamnosus comparative strain (third plate) or together with Lb. rhamnosus CHCC15871 (fourth column). The plates had been incubated at 7±1° C. for 26 days. The target contaminant, Rhodotorula mucilaginosa, was added in concentrations of $1 \times 10^3$ cfu/spot (top row), $1 \times 10^2$ cfu/spot (middle row) and $1 \times 10^1$ cfu/spot (bottom row).

As will appear from the results of the yeast agar-assay presented in FIGS. 3 and 4, the tested yeasts grew very well on the agar plates made from milk fermented only with the starter culture (reference). However, when Lb. rhamnosus CHCC15871 was present during milk fermentation the resulting plates inhibited growth of all of the yeasts tested. The level of inhibition was even higher than the inhibition observed for the commercial bioprotective strain, Lb. rhamnosus CHCC12483, and for the Lb. comparative strain.

Figure 5:
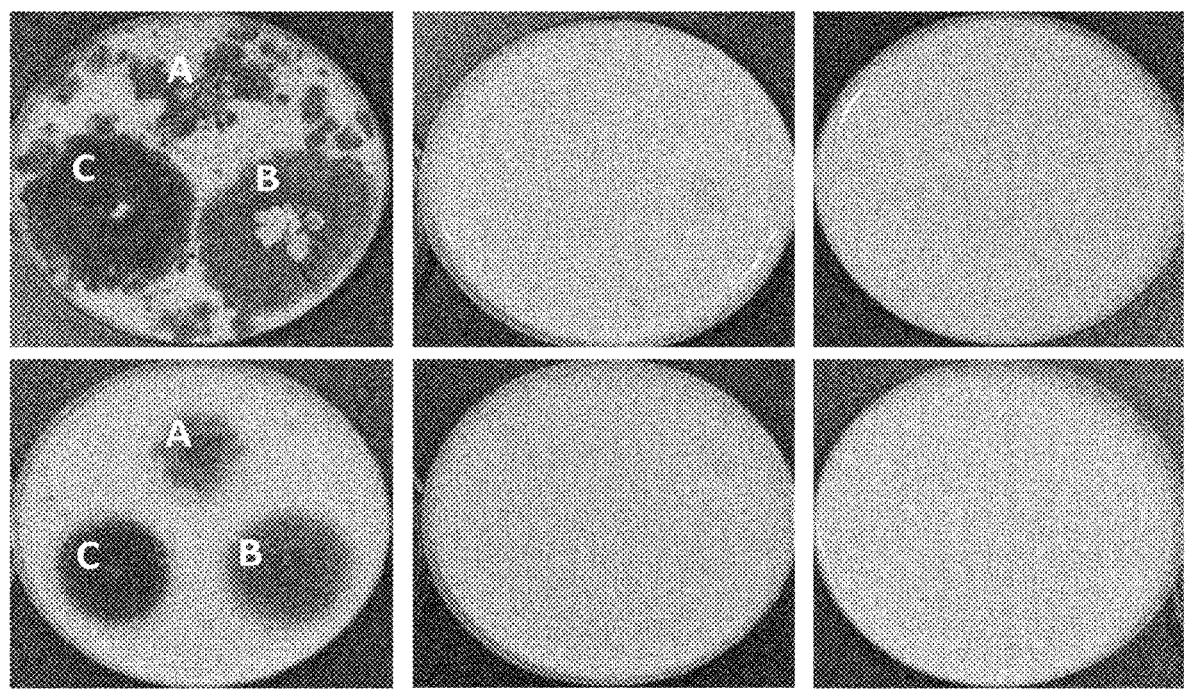
FIG. 5 shows the growth of molds on plates prepared from milk fermented with a starter culture alone (reference, first plate) or together with Lb. rhamnosus CHCC12483 (second plate) or together with Lb. rhamnosus CHCC15871 (third plate) for 3 different mold contaminants A, B and C and for 2 different temperatures (upper and lower row of plates).

FIG. 5 shows the growth of molds on plates prepared from milk fermented with a starter culture alone (reference, first plate) or together with Lb. rhamnosus CHCC12483 (second plate) or together with Lb. rhamnosus CHCC15871 (third plate). The plates had been incubated at 25±1° C. for 12 days (top row) or 7±1° C. for 27 days (bottom row). The target contaminants were added in concentrations of 500 spores/spot: (A) Penicillium brevicompactum, (B) Penicillium crustosum and (C) Penicillium solitum.

FIG. 5 shows that all of the tested molds were able to grow on the agar plates made from milk fermented only with the starter culture (reference). When Lb. rhamnosus CHCC12483 was present during milk fermentation, the growth of the molds was inhibited. When Lb. rhamnosus CHCC15871 was present during milk fermentation, the growth of the molds was inhibited even stronger than for CHCC12483.

Example 2: Effect of Lb. Rhamnosus Strain CHCC15871 on Post-Acidification

Lb. rhamnosus strain (CHCC15871) was tested for the influence of acidification speed and on effect on post-acidification.

Reduced-fat (1.5% w/v) homogenized milk was heat-treated at 90±1° C. for 20 min and cooled immediately. A commercial yogurt starter culture (F-DVS YoFlex Mild 2.0) was inoculated at 0.02% (v/w), and the inoculated milk was distributed into 200 ml bottles. One bottle was inoculated with Lb. rhamnosus CHCC15871 in total concentration of $1 \times 10^7$ CFU/g, one bottle was inoculated with Lb. rhamnosus CHCC12483, and the commercial bioprotective strain (isolated from Holdbac® YM-B) in total concentration of $1 \times 10^7$ CFU/g, and one bottle was used as a reference and only inoculated with the starter culture. All bottles were incubated in a water bath at 43±1° C. and fermented at these conditions until pH of 4.60±0.1 was reached. After fermentation, the bottles were vigorously shaken to break the coagulum and cooled on ice.

To monitor the effect on post acidification, the three fermented milk samples (starter-only, Lb. rhamnosus CHCC12483, and Lb. rhamnosus CHCC15871) were stored at 7±1° C. for 21 days and pH was measured on day 1, 7, 14 and 21.

Figure 6:
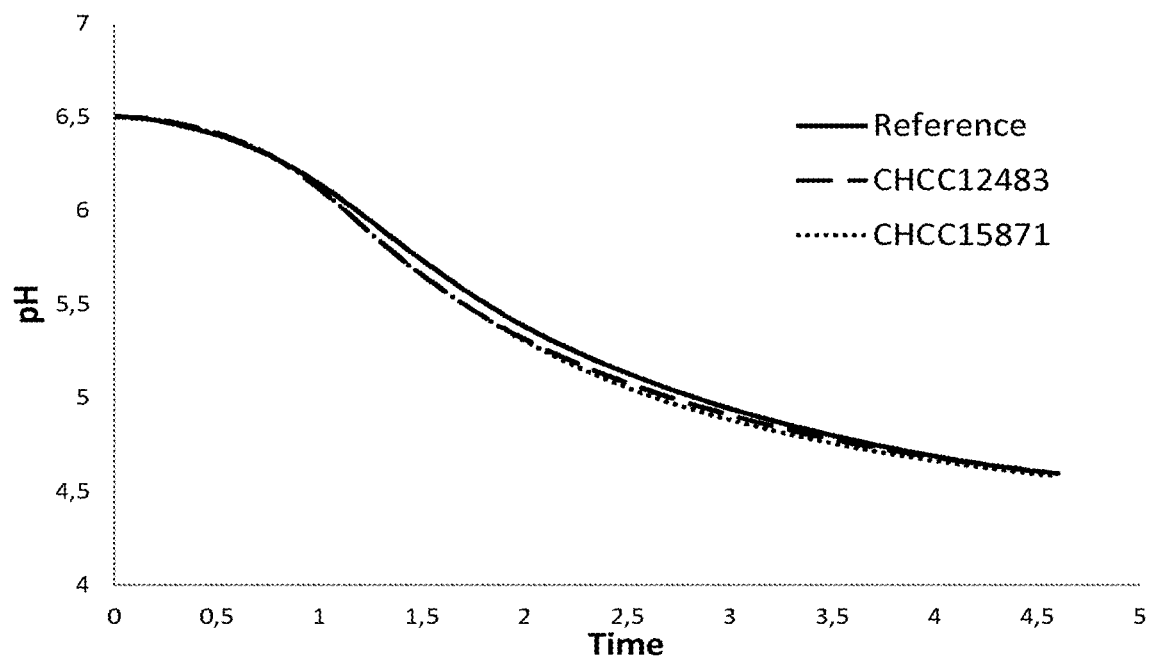
FIG. 6 shows the acidification profile of fermented milk products during fermentation at 43° C. The products are fermented with starter culture only, Reference, or starter culture in combination with Lb. rhamnosus CHCC12483 or Lb. rhamnosus CHCC15871 strains.

FIG. 6 shows the acidification profile of fermented milk products during fermentation at 43° C. The products are fermented with starter culture only, Reference, or starter culture in combination with Lb. rhamnosus CHCC12483 or Lb. rhamnosus CHCC15871 strains.

As will appear from FIG. 6, the addition of neither of the two Lb. rhamnosus strains changed the acidification profile of the fermentation.

Figure 7:
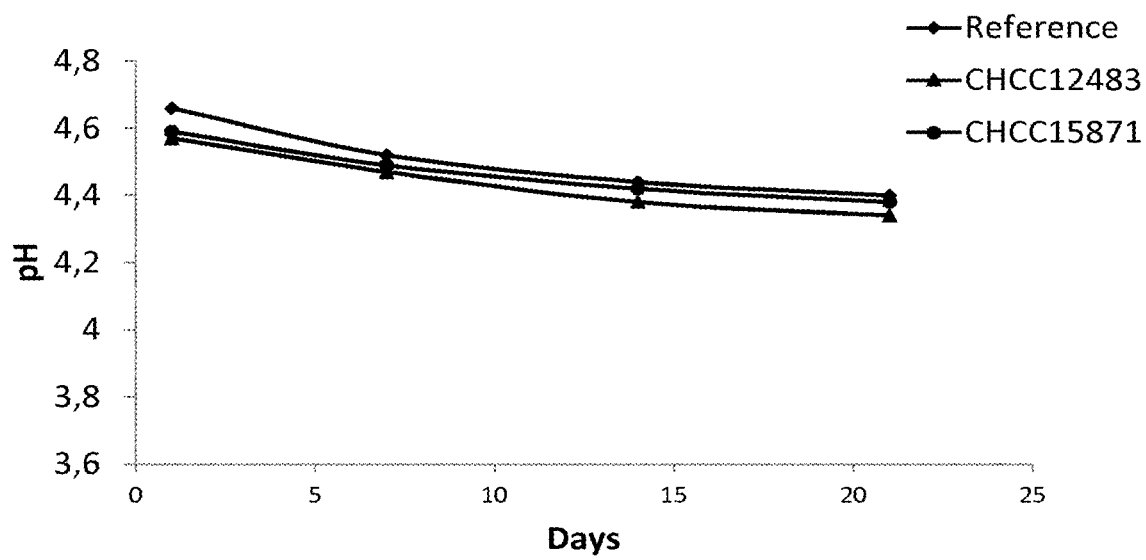
FIG. 7 shows the pH development in fermented milk products over time when stored at 7±1° C. for 21 days. The products are fermented with starter culture only, Reference, or starter culture in combination with Lb. rhamnosus CHCC12483 or Lb. rhamnosus CHCC15871 strains.

FIG. 7 shows the pH development (post-acidification) in fermented milk products over time when stored at 7±1° C. for 21 days. The products are fermented with starter culture only, Reference, or starter culture in combination with Lb. rhamnosus CHCC12483 or Lb. rhamnosus CHCC15871 strains.

As will appear from FIG. 7, the addition of neither of the two Lb. rhamnosus strains changed the post-acidification properties of the fermented milk products to any significant degree.

Example 3: Semi-Quantitative Analysis of the Inhibitory Effect of Lb. Rhamnosus CHCC15871 Against Different Mold Contaminants For the semi-quantitative analysis of the inhibitory effect of Lb. rhamnosus CHCC15871, an agar-assay was used, resembling the manufacturing process and product of sour cream:

Standardized milk (9% fat w/v) homogenized milk was heat-treated at 90±1° C. for 20 min and cooled immediately. A commercial sour cream starter culture (F-DVS XT-314) was inoculated at 0.02% (v/w), and the inoculated milk was distributed into 200 ml bottles. One bottle was inoculated with Lb. rhamnosus CHCC15871 in total concentration of $5 \times 10^6$ CFU/g and one bottle was used as a reference and only inoculated with the starter culture. Both bottles were incubated in a water bath at 26±1° C. and fermented at these conditions until pH of 4.60±0.1 was reached. After fermentation, the bottles were vigorously shaken to break the coagulum and cooled on ice. Then the fermented milk was warmed to a temperature of 40° C. and added 40 ml of a 5% sterile agar solution that had been melted and cooled down to 60° C. This solution of fermented milk and agar was then poured into sterile Petri dishes and the plates were dried in a LAF bench for 30 min.

Spore suspension of three different molds were spotted in concentration of 500 spores/spot; Penicillium brevicompactum (DSM 32094), P. crustosum and P. solitum (DSM 32093). The three molds were spotted on the same plate. Plates were incubated at 25±1° C. and regularly examined for the growth of molds.

Figure 8:
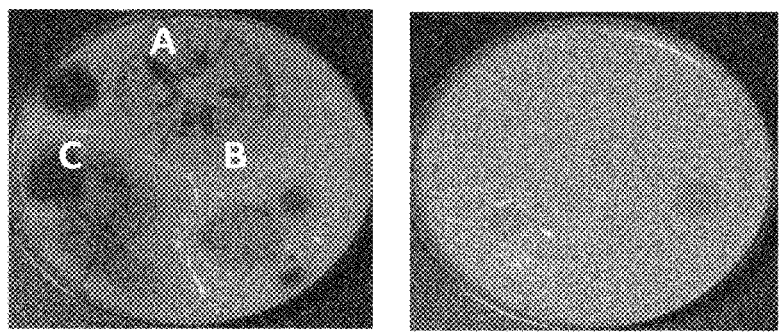
FIG. 8 shows the growth of molds on plates prepared from milk fermented with a starter culture alone (reference, first plate) or together with Lb. rhamnosus CHCC15871 (second plate) for 3 different mold contaminants A, B and C.

FIG. 8 shows the growth of molds on plates prepared from milk fermented with a starter culture alone (reference, first plate) or together with Lb. rhamnosus CHCC15871 (second plate). The plates had been incubated at 25±1° C. for 12 days. The target contaminants were added in concentrations of 500 spores/spot: (A) Penicillium brevicompactum, (B) Penicillium crustosum and (C) Penicillium solitum.

FIG. 8 shows that all of the tested molds were able to grow on the agar plates made from milk fermented only with the starter culture (reference). When Lb. rhamnosus CHCC15871 was present during milk fermentation, the growth of the molds was strongly inhibited.

Example 4: Effect of Lb. Rhamnosus Strain CHCC15871 on Diacetyl and Acetoin Production, Fermentation Time and Viscosity The Lb. rhamnosus strain (CHCC15871) was tested for the effect on diacetyl and acetoin production, fermentation time and viscosity in sour cream application. The performance was compared to a conventional Lb. rhamnosus CHCC12697 known to have a high diacetyl production, cf. WO2012/136832, and antifungal activity, cf. WO2012/136830.

Sour cream base (18% fat and 2.7% protein w/v) was homogenized (two steps 200/70 bars at 70° C.), heat-treated at 85±1° C. for 3 min and cooled immediately. At trial start the sour cream base was distributed into 200 ml sterile bottles. Five starter cultures (SC1-SC5)—consisting of Lactococcus lactis subsp. lactis, Lactococcus lactis subsp. cremoris, Streptococcus thermophilus and Leuconostoc— were inoculated at 0.01% (v/w). Five bottles per starter culture were inoculated. Two bottles were furthermore inoculated with Lb. rhamnosus CHCC15871 in total concentration of $5 \times 10^6$ CFU/g, and another two bottles with Lb. rhamnosus CHCC12697 (basis of comparison) in total concentration of $5 \times 10^6$ CFU/g. One bottle per starter culture served as reference/control. All bottles were incubated in a water bath at 30±1° C. and fermented at these conditions until pH of 4.50±0.1 was reached. At end pH, the coagulum was stirred (20 times with hand stirrer) to reach homogenous texture and cooled on ice. After cooling the bottles were stored at 5±1° C.

Figure 9:
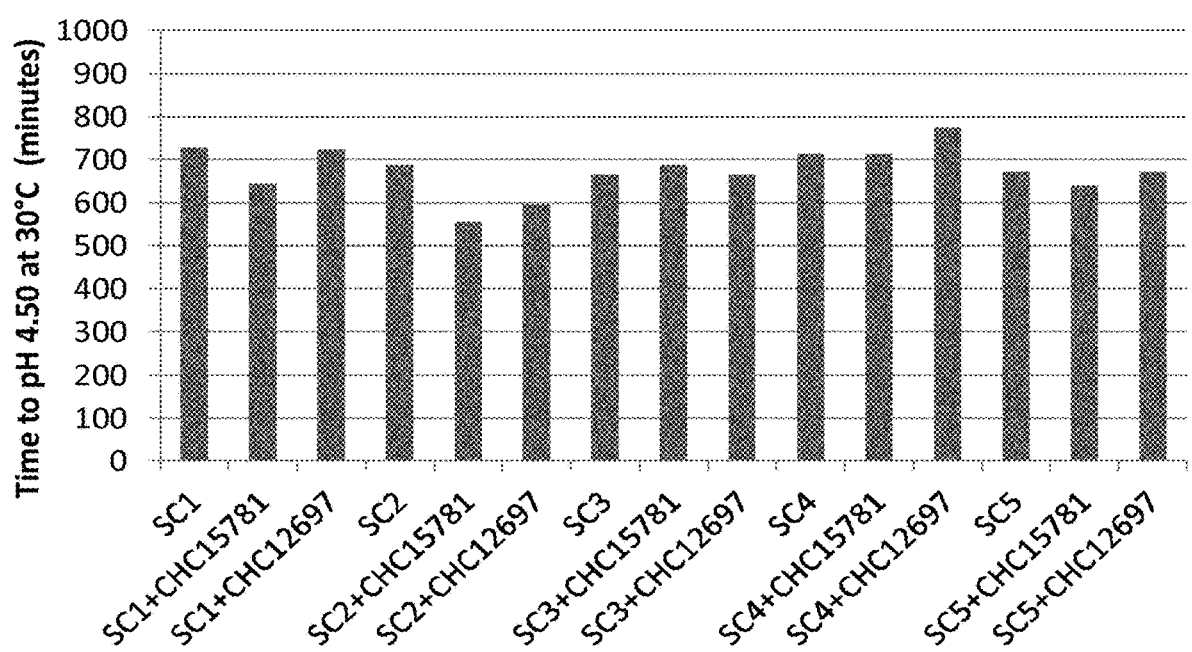
FIG. 9 shows the fermentation time (in minutes) to end pH 4.50 at 30° C. The products are fermented with five different sour cream starter culture (SC1-SC5) alone and in combination with Lb. rhamnosus CHCC15871 or Lb. rhamnosus CHCC12697 strains.

The registered fermentation times are illustrated in FIG. 9. Importantly, the combination with Lb. rhamnosus strains does not cause significantly increased fermentation times. For SC1, SC2, SC4 and SC5, the fermentation time with mixtures of starter culture and CHCC15871 were lower than those of starter culture alone and of starter culture and CHCC12697.

On day 7 and 21 samples were analyzed for diacetyl and acetoin by static head space gas chromatography (HSGC), a sensitive method for analyzing volatiles in complex matrices. The setup consisted of a Static Head Space sampler connected to Gas Chromatograph with Flame Ionization Detector (FID). For that purpose the following equipment was used:

- HS-autosampler: HS40XI, TurboMatrix 110, Perkin Elmer
- HS-software: HSControl v.2.00, Perkin Elmer
- GC: Autosystem XL, Perkin Elmer
- GC-software: Turbochrom navigator, Perkin Elmer
- Column: HP-FFAP 25 m×0.20 mm×0.33μη, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 μl of 4N $H_2SO_4$ to 1 g fermented sour cream sample and analyzed by HSGC.

Figure 10:
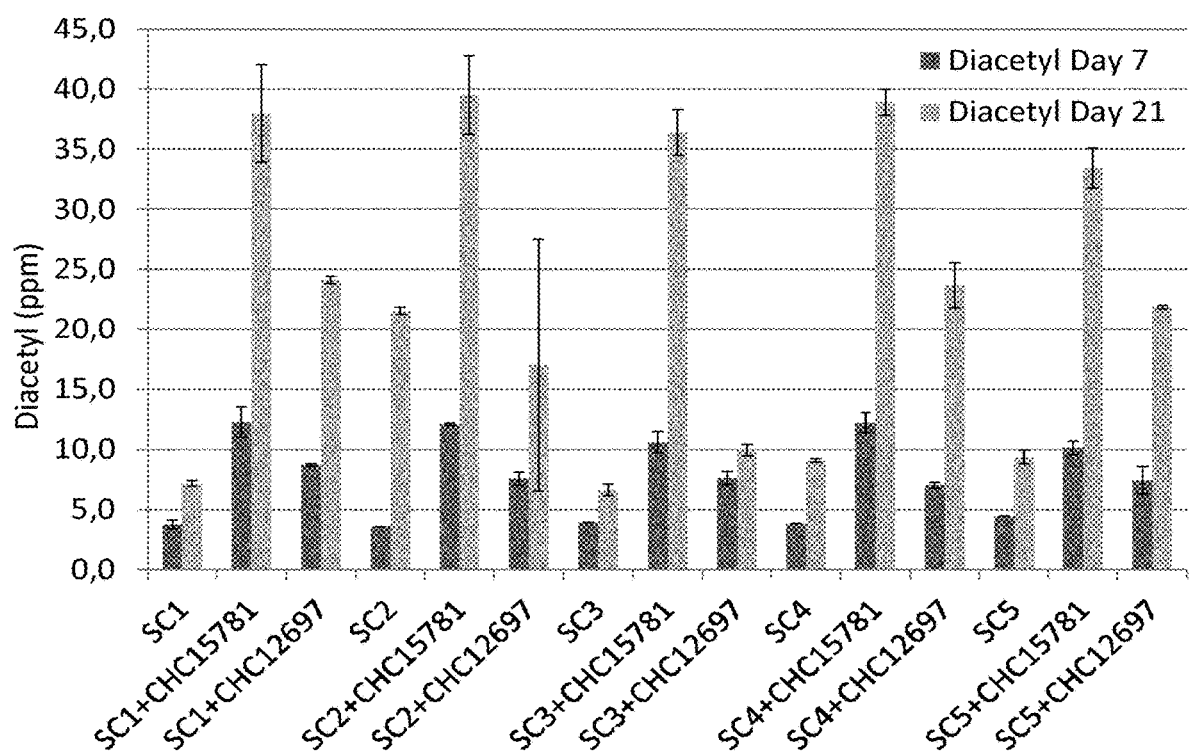
FIG. 10 shows the diacetyl levels (ppm, average+/−std deviation) after storage at 5±1° C. for 7 and 21 days in fermented sour cream products fermented with five different starter cultures (SC1-SC5) alone and in combination with Lb. rhamnosus CHCC15871 or Lb. rhamnosus CHCC12697 strains.
Figure 11:
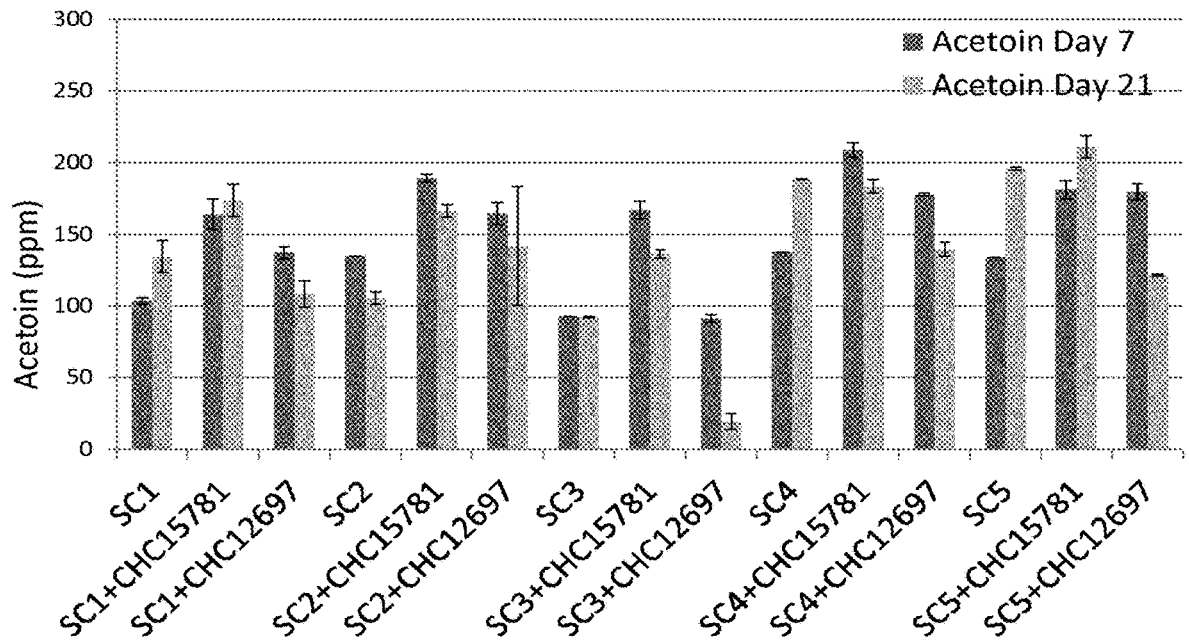
FIG. 11 shows the acetoin levels (ppm, average+/−std deviation) after storage at 5±1° C. for 7 and 21 days in fermented sour cream products fermented with five different starter cultures (SC1-SC5) alone and in combination with Lb. rhamnosus CHCC15871 or Lb. rhamnosus CHCC12697 strains.

The effect on diacetyl production is illustrated in FIG. 10 and for acetoin in FIG. 11. FIG. 10 shows that addition of *Lb. rhamnosus* CHCC15871 during fermentation has a very high effect on the amount of produced diacetyl, especially after 21 days of cold storage and surprisingly, the amounts are significantly higher compared to samples with *Lb. rhamnosus* CHCC12697. Furthermore, CHCC15871 also produces higher levels of acetoin compared to CHCC12697 as illustrated in FIG. 11.

Seven days after production, the fermented sour cream product was brought to 13° C. and stirred manually (20 times) until homogeneity of the sample. The rheological properties of the sample were assessed on a rheometer (Anton Paar Physica Rheometer with ASC, Automatic Sample Changer, Anton Paar® GmbH, Austria) by using a bob-cup geometry. The rheometer was set to a constant temperature of 13° C. during the time of measurement. Settings were as follows:

Holding time (to rebuild to somewhat original structure) 5 minutes without any physical stress (oscillation or rotation) applied to the sample.

Rotation step (to measure shear stress at 300 Vs)

Two steps were designed:

1) Shear rate=[0.3-300] 1/s and 2) Shear rate=[275-0.3] 1/s. Each step contained 21 measuring points over 210 s (on every 10 s).

0 The shear stress at the peak point (300 1/s) of the flow curves were chosen for further analysis as this value has shown to correlate well with the perceived mouth thickness. Shear stress (Pa) is given as Viscosity (Pa*s)*Shear rate (1/s).

Figure 12:
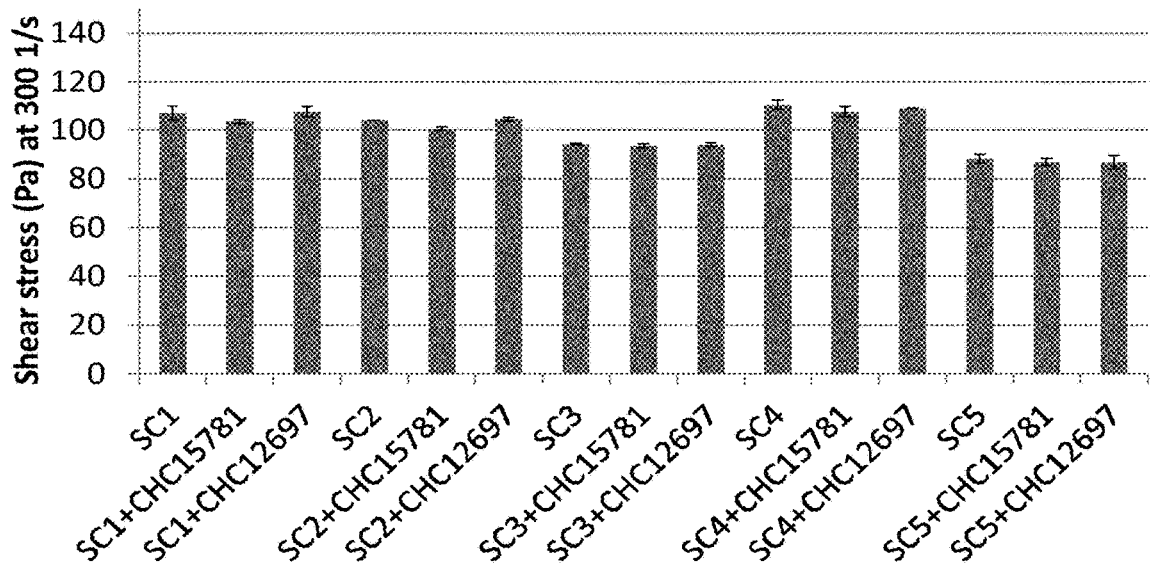
FIG. 12 shows the rheological measurement of fermented sour cream products after storage at 5±1° C. for 7 days. Shear stress (Pa, average+/−std deviation) at 300 shear rate (Vs) derived from flow curve data. Samples fermented with five different starter cultures (SC1-SC5) alone and in combination with Lb. rhamnosus CHCC15871 or Lb. rhamnosus CHCC12697 strains.

FIG. 12 illustrates rheological results. Clearly, the addition of *Lb. rhamnosus* strains has no negative effect on texture properties expressed by shear stress at 300 shear rate. Shear stress does not decrease compared to reference samples (SC1-SC5).

Example 5: Comparison Diacetyl Production of *Lb. Rhamnosus* CHCC15871 with Different *Lb. Rhamnosus* Strains Diacetyl production of *Lb. rhamnosus* CHCC15871 strain with seven different *Lb. rhamnosus* strains.

Reduced-fat (1.5% w/v) homogenized milk was heat-treated at 90±1° C. for 20 min and cooled immediately. A commercial yogurt starter culture (F-DVS YoFlex Mild 2.0) was inoculated at 0.02% (v/w), and the inoculated milk was distributed into 200 ml bottles. 8 bottles were inoculated with *Lb. rhamnosus* strains (CHCC15871, CHCC12483, strain 1, strain 2, strain 3, strain 4, strain 5 and strain 6) in total concentration of $1 \times 10^7$ CFU/g, one strain per bottle. One bottle was used as a reference and only inoculated with the starter culture. All bottles were incubated in a water bath at 43±1° C. and fermented at these conditions until pH of 4.55±0.1 was reached. After fermentation, the bottles were vigorously shaken to break the coagulum and cooled on ice. After cooling samples were stored at 7±1° C.

On day 14 samples were analyzed for diacetyl by static head space gas chromatography (HSGC), a sensitive method for analyzing volatiles in complex matrices. The setup consisted of a Static Head Space sampler connected to Gas Chromatograph with Flame Ionization Detector (FID). For that purpose, the following equipment was used:

- HS-autosampler: HS40XI, TurboMatrix 110, Perkin Elmer
- HS-software: HSControl v.2.00, Perkin Elmer
- GC: Autosystem XL, Perkin Elmer
- GC-software: Turbochrom navigator, Perkin Elmer
- Column: HP-FFAP 25 m×0.20 mm×0.33μη, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 μl of 4N H2SO4 to 1 g yoghurt sample and immediately analyzed by HSGC.

Figure 13:
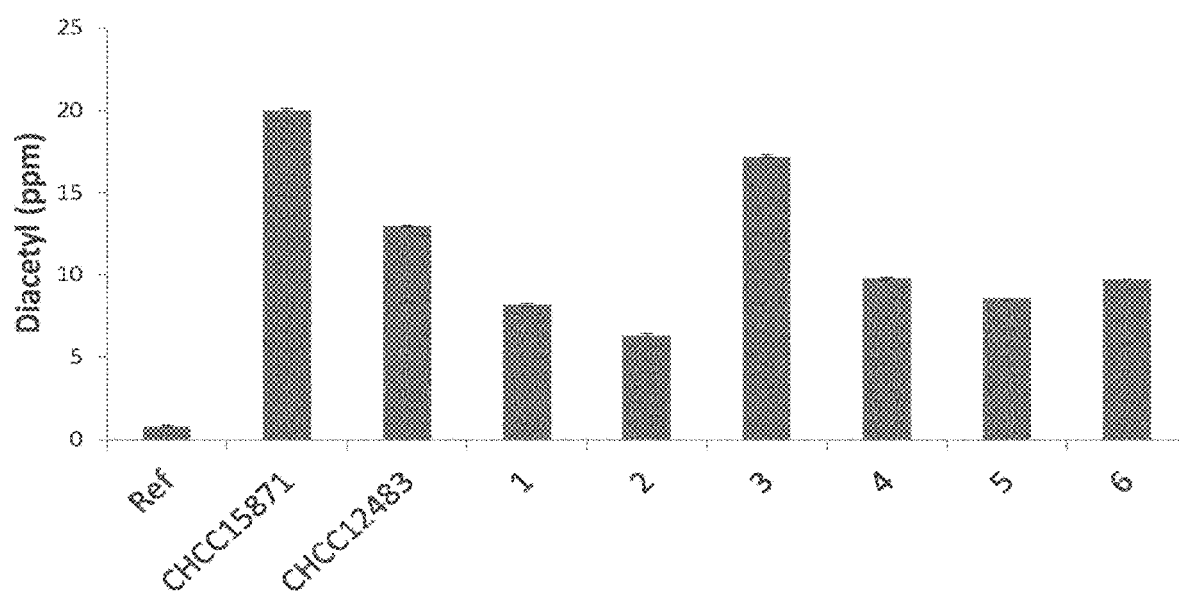
FIG. 13 shows the diacetyl levels (ppm, average+/−std deviation) after storage at 7±1° C. for 14 days in yogurt products fermented with starter culture alone and in combination with 8 different Lb. rhamnosus strains (CHCC15871, CHCC12483, strain 1, strain 2, strain 3, strain 4, strain 5 and strain 6).

The effect on diacetyl production is illustrated in FIG. 13, showing that the addition of the seven different *Lb. Rhamnosus* strains during the fermentation resulted in varying levels of diacetyl present in the samples after 14 days of storage. Observed levels vary between 6.3 ppm and 20 ppm. CHCC15871 produced highest amount of diacetyl in comparison.

DEPOSITS and EXPERT SOLUTION

The applicant requests that a sample of the deposited micro-organisms stated below may only be made available to an expert, until the date on which the patent is granted.

The *Lactobacillus rhamnosus* strain CHCC15871 was deposited on 2017 Oct. 17 at the German Collection of Microorganisms and Cell Cultures (Deutsche Sammlung von Mikroorganismen und Zellkulturen GmbH; DSMZ), Inhoffenstr. 7B, D-38124 Braunschweig and given the accession No.: DSM 32666.

The *Lactobacillus rhamnosus* strain CHCC15860 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: DSM 32092.

The *Lactobacillus rhamnosus* strain CHCC12697 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2011 Mar. 1 under the accession No.: DSM 24616.

The *Penicillium solitum* strain CHCC16948 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: DSM 32093.

The *Penicillium brevicompactum* strain CHCC16935 was deposited at German Collection of Microorganisms and Cell Cultures (Deutsche Sammlung von Mikroorganismen and Zellkulturen GmbH; DSMZ), Inhoffenstr. 7B, D-38124 Braunschweig deposited on 2015 Jul. 16 under the accession No.: DSM 32094.

The deposits were made according to the Budapest treaty on the international recognition of the deposit of microorganisms for the purposes of patent procedure.

REFERENCES

Jyoti, B. D., Suresh, A. K., and Venkatesh, K. V. (2003): Diacetyl production and growth of *Lactobacillus rhamnosus* on multiple substrates. World Journal of Microbiology & Biotechnology 19: 509-514.

The invention claimed is:

1. A composition comprising (i) bacteria of *Lactobacillus rhamnosus* strain CHCC15871 deposited with the German Collection of Microorganisms and Cell Cultures (DSMZ) under Accession No. DSM 32666, or a mutant strain thereof, wherein the mutant strain is obtained by using the deposited strain as a mother strain and wherein the mutant strain has the same or a higher diacetyl production as compared to the mother strain, and (ii) a cryoprotectant.

2. The composition according to claim 1, further comprising bacteria of at least one further lactic acid bacterium strain.

3. The composition according to claim 1, wherein the bacteria of at least one further lactic acid bacterium strain comprises bacteria of at least one anti-fungal lactic acid bacterium strain selected from the group consisting of a *Lactobacillus rhamnosus* strain, a *Lactobacillus fermentum* strain, a *Lactobacillus paracasei* strain, a *Lactobacillus plantarum* strain, a *Propionibacteria freudenreichii* strain, a *Pediococcus acidilactici* strain, a *Enterococcus faecium* strain, and a *Lactococcus lactis* strain.

4. The composition according to claim 3, wherein the bacteria of at least one antifungal lactic acid bacterium strain comprises bacteria of *Lactobacillus rhamnosus* strain CHCC15860 deposited at German Collection of Microorganisms and Cell Cultures (DSMZ) under Accession No. DSM 32092.

5. The composition according to claim 1, wherein the composition further comprises a starter culture for producing a fermented milk product comprising one or more strains selected from the group consisting of the genera *Lactococcus*, *Streptococcus* and *Lactobacillus*.

6. The composition according to claim 1, wherein the composition comprises the bacteria in a form selected from the group consisting of a frozen concentrate, a dried concentrate, and a freeze-dried concentrate.

7. The composition according to claim 1, wherein the cryoprotectant comprises one or more selected from mannitol, sorbitol, sodium tripolyphosphate, xylitol, glycerol, raffinose, maltodextrin, erythritol, threitol, trehalose, glucose, and fructose.

8. The composition according to claim 1, further comprising one or more additives selected from yeast extracts, sugars, vitamins, carbohydrates, flavors, minerals, and enzymes.

9. The composition according to claim 6, comprising viable cells of the bacteria in an amount from $10^4$ to $10^{12}$ colony forming units (CFU) per gram of composition.

10. The composition according to claim 1, in a liquid form comprising a suspension of the bacteria in a liquid medium.

11. The composition according to claim 10, comprising viable cells of the bacteria in an amount from $10^4$ to $10^{12}$ colony forming units (CFU) per ml of composition.

12. The composition according to claim 5, wherein the one or more strains selected from the group consisting of the genera *Lactococcus*, *Streptococcus* and *Lactobacillus* comprise one or more strain selected from a *Lactobacillus bulgaricus* strain, a *Streptococcus thermophilus* strain, and a *Lactococcus lactis* strain.

13. The composition according to claim 5, wherein the starter culture exhibits increased resistance to growth of one or more of yeasts and molds as compared to a starter culture prepared without the *Lactobacillus rhamnosus* strain.

* * * * *